United States Patent [19]

Giersch et al.

[11] Patent Number: 4,608,445
[45] Date of Patent: Aug. 26, 1986

[54] OXYGENATED ALICYCLIC COMPOUNDS

[75] Inventors: Wolfgang K. Giersch, Bernex; Karl H. Schulte-Elte, Onex; Günther Ohloff, Bernex, all of Switzerland

[73] Assignee: Firmenich SA, Geneva, Switzerland

[21] Appl. No.: 443,960

[22] Filed: Nov. 23, 1982

[30] Foreign Application Priority Data

Dec. 10, 1981 [CH] Switzerland ......................... 7888/81

[51] Int. Cl.[4] .................. C07C 43/184; C07C 43/188
[52] U.S. Cl. .................................... 568/667; 568/670; 252/522 R; 131/276
[58] Field of Search ................................ 568/667, 670

[56] References Cited

FOREIGN PATENT DOCUMENTS 2395751 1/1979 France.
2418214 9/1979 France.

OTHER PUBLICATIONS

Palfray et al., Chem. Abs., vol. 28 (1934) 5407.
Eliel et al., Jour. Amer. Chem. Soc., vol. 84 (1962) 2371-2377.

*Primary Examiner*—Bernard Helfin
*Attorney, Agent, or Firm*—Pennie & Edmonds

[57] ABSTRACT

The compounds of formula $$X-CH_2-CH(OH)-CH_2-R \qquad (I)$$

wherein symbol R represents a $C_1$-$C_3$ alkyl radical and X a substituted cyclohexyloxy group of formula

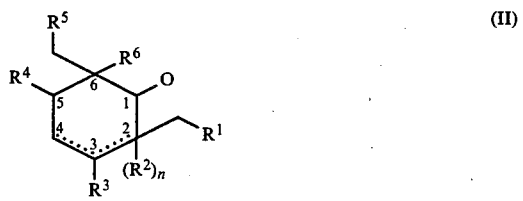

(II)

wherein index n stands for zero or one, the dashed lines indicate a single bond (n=1) or a double bond in position 2 (n=0) or 3 (n=1) and each of symbols $R^1$ to $R^6$ designates a hydrogen atom or a methyl radical, are new and can be conveniently utilized as perfuming and flavoring ingredients. They develop in particular woody-ambery notes.

2 Claims, No Drawings

OXYGENATED ALICYCLIC COMPOUNDS

BRIEF SUMMARY OF THE INVENTION

The instant invention relates to novel compounds of formula

X—CH$_2$—CH(OH)—CH$_2$—R    (I)

wherein symbol R represents a C$_1$–C$_3$ alkyl radical and X a substituted cyclohexyloxy group of formula

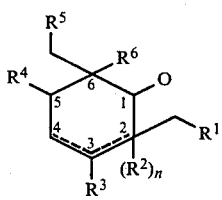

wherein index n stands for zero or one, the dashed lines indicate a single bond (n=1) or a double bond in position 2 (n=0) or 3 (n=1) and each of symbols R$^1$ to R$^6$ designates a hydrogen atom or a methyl radical.

This invention relates also to a process for the preparation of compounds (I) which process makes use as starting materials of the compounds of formula (IV)

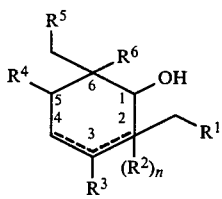

wherein the dashed lines, index n and symbols R$^1$ to R$^6$ have above given meaning, and of formula

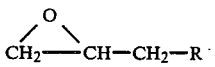

wherein R represents a C$_1$ to C$_3$ alkyl radical.

The present invention provides further a perfuming or a flavoring composition containing as active ingredient a compound of formula (I).

This invention provides further a perfumed product or a foodstuff, a beverage, a pharmaceutical preparation or a tobacco product containing as active perfuming or flavoring ingredient a compound of formula (I).

BACKGROUND OF THE INVENTION

Certainly, one of the most widely examined class of odorants is represented by the woody compounds. This class consists of chemicals of very different nature and includes alcohols, esters, ketones and ethers having mono- or polycyclic structure, as well as macrocyclic derivatives. Among the woody odorants possessing an alicyclic structure, one may cite the aliphatic ether derivative of ionones, such as for example the compounds of formula

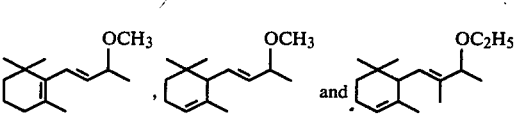

which develop an overall woody odor accompanied by a fruity, ambery or, in certain instances, tobacco-like tonality (see DE-OS No. 2,827,636).

Several methyl homologs of β-ionone are disclosed by S. Arctander in Perfume and Flavor Chemicals (Montclair, N.J. 1969, sections 2087 and 2088).

Alicyclic alcohol of formula

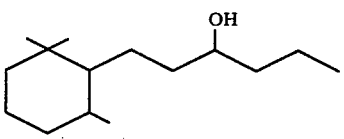

is known to possess fixative properties in perfumes and it develops an odor of woody-ambery type (see DE-OS No. 2,807,584).

Strange as it may seem, an analogous class of compounds has remained sofar unrecognized. We have now discovered that oxygenated alicyclic derivatives of formula (I) develop useful organoleptic properties and that consequently they can be used as valuable ingredients in the perfume and the flavor industry.

PREFERRED EMBODIMENTS OF THE INVENTION

In the field of fragrances, compounds (I) are characterized by an elegant, warm and clinging woody-ambery scent enriched by a slightly animal tonality reminiscent of natural amber; in some instances, their odor can also be fruity or flowery. Compounds (I) are powerful and show medium tenacity. They are especially suitable for manufacturing fragrance compositions of various nature, such as for instance chypre, rosy, woody or fougère type compositions, to which they confer harmony and richness without however destroying the desired balance of their woody-ambery tonality.

Compounds (I) can be utilized successfully for the manufacture or perfumed products such as soaps, detergents, household materials and cosmetics, namely cosmetics for men-lines such as colognes or after-shave lotions.

The proportions necessary to achieve the desired effects can vary within a wide range of values. The experts in the art realize that those values depend on the nature of the coingredients used in a given composition and on the nature of the products to which they are added. Typically, concentrations of the order of 1 to 25%, or even 30% by weight in the case of perfume bases or concentrates, can be used.

In the field of flavors, compounds of formula (I) are characterized by a taste and an aroma which may be defined as being woody and ambery. Due to their gustative properties, compounds (I) are particularly adapted to the aromatization of tobacco or tobacco products. They can be used to confer the typical aroma character of oriental tobacco blends.

The compounds of the invention, or the compositions containing them, may be used in a variety of forms, but they are preferably used in solution. The form in which a given compound is best employed will depend upon its chemical nature, solubility and stability. Flavoring can occur in any step of the manufacturing process. In tobacco aromatization for instance, the flavor can be added at any step of tobacco treatment during aging, drying or curing before actual cigarettes manufacture. A convenient method for flavoring tobacco consists in spraying it with an alcoholic solution of the compound or flavoring composition. As an alternative to alcohol, a mixed solvent may be used for this purpose, such as a mixture of alcohol and propylene glycol.

The proportions in which the flavoring agent of the invention are used can vary-widely, depending upon the type of product to which they are added and the specific organoleptic effect it is desired to achieve. For example, interesting flavoring effects can be achieved with amounts ranging from 1 to 100 ppm (parts by weight per million), based on the weight of the product flavored. Typically, proportions from 5 to 10 ppm are preferred; but in all cases, these ranges can be varied in order to achieve specific effects.

According to the invention, the compounds of formula (I) can be prepared from alicyclic alcohols of formula

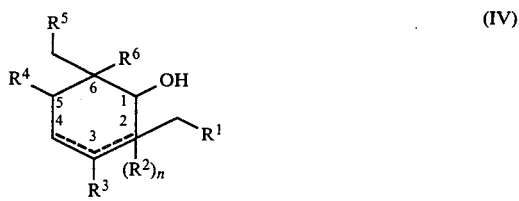

wherein symbols $R^1$ to $R^6$, index n and the dashed lines are defined as indicated above for formula (I), by reacting them with a compound of formula

wherein symbol R represents a $C_1$ to $C_3$ alkyl radical.

According to the process of the invention, the reaction is carried out in the presence of a strong base such as an alkali metal hydride, for example sodium or lithium hydride, or an alkali metal, for example sodium. Moreover, the reaction is effected in the presence of an inert organic solvent such as an ether or an aliphatic or aromatic hydrocarbon, e.g. petrol ether or toluene (see in this respect: Houben-Weyl, Methoden der Organischen Chemie, Georg Thieme Verlag, Stuttgart 1965, Vol. VI/3).

Alicyclic alcohols of formula (IV) used as starting materials for the process of the invention are either commercial products or, in the alternative, they can be prepared by reducing the corresponding available ketones according to current techniques.

Compounds (I), as directly obtained by the process of the invention, occur in various stereoisomeric form according to the nature of the different substituents on the six-membered ring. The differend isomers may be seperated by means of the usual techniques, for instance by preparative vapour phase chromatography. Though characterized by their main typical woody-ambery smell, different isomers possess different odor nuances. For all practical purposes however, it is preferred to use the mixture of isomers as directly obtained by the above described process.

The invention is better illustrated by but not limited to the following examples (the temperatures are indicated in degrees centigrade).

EXAMPLE 1

1-(2,6,6-Trimethyl-cyclohex-1-yloxy)-pentan-2-ol

A mixture of 2.0 g of 2,6,6-trimethyl-cyclohexanol and 0.354 g of sodium hydride was heated for 24 hours at 80° in 10 ml of anhydrous toluene. 1.2 G of 1,2-epoxy-pentane were then added to the thus obtained solution and heating at 80° was maintained for 24 additional hours. After cooling, the reaction mixture was poured onto crushed iced, acidified with diluted $H_2SO_4$, whereupon the organic phase was washed with brine until neutrality. After evaporation of the volatile parts and distillation of the residue in a a bulb apparatus (bath temperature: 140°/7 Pa), the desired product was obtained in yield of about 75%. An analytical sample was purified by preparative gas chromatography.

IR: 3450 $cm^{-1}$;

NMR: signals at 1.0; 1.2-1.6; 2.5; 2.8; 3.4 and 3.75 δ ppm;

MS: $M^+$=228(68); m/e: 157(25), 142(20), 125(45), 109(29), 95(16), 82(69), 69(100), 55(38), 41(48).

Olfactive evaluation: woody-ambery; powerful, clinging; weak animal note of natural amber.

EXAMPLE 2

By following the same procedure as that described in Example 1, the following compounds were prepared:

(a) 1-(2,6,6-trimethyl-cyclohex-1-yloxy)-butan-2-ol

Starting materials;
  2,6,6-trimethyl-cyclohexanol
  1,2,epoxy-butane.

IR: 3430 $cm^{-1}$;

NMR: signals at 1.0; 2.5; 2.8 and 3.4-4.0 δ ppm;

MS: $M^+$=214(99); m/e: 143(45), 125(53), 109(37), 95(22), 82(90), 69(100), 55(66), 41(51).

Olfactive evaluation: woody-ambery; moderately powerful.

(b) 1-(2,6,6-trimethyl-cyclohex-2-en-1-yloxy)-butan-2-ol

Starting materials:
  2,6,6-trimethyl-cyclohex-2-en-1-ol
  1,2-epoxy-butane.

NMR: signals at 0.88, 0.97, 0.98, 1.78; 2.5; 3.13; 3.4-3.75 and 5.43 δ ppm;

MS: $M^+$=212(1); m/e: 156(103), 123(35), 107(21), 84(100), 73(40), 57(39), 43(63).

Olfactive evaluation: woody, leathery; weak ambery-animal and saffron note.

(c) 1-(2,6,6-trimethyl-cyclohex-2-en-1-yloxy)-pentan-2-ol

Starting materials:
  2,6,6-trimethyl-cyclohex-2-en-1-ol
  1,2-epoxy-pentane.

NMR: signals at 0.88; 0.93; 0.97; 1.79; 2.45; 3.13; 3.4-4.0 and 5.46 δ ppm;

MS: m/e: 170(52), 123(28), 107(12), 84(100), 69(11), 55(16), 41(23).

Olfactive evaluation: woody, slightly fruity; slightly cellar-like.

(d)
1-(2,6,6-trimethyl-cyclohex-3-en-1-yloxy)-pentan-2-ol

Starting materials:
2,6,6-trimethyl-cyclohex-3-en-1-ol
1,2-epoxy-pentane.
NMR: signals at 1.0; 2.5; 2.92; 3.3–4.0 and 5.2–5.6 δ ppm;
MS: m/e: 158(72), 123(13), 107(8), 97(4), 87(16), 72(100), 55(14), 41(22).

Olfactive evaluation: typical woody-ambery; powerful.

(e) 1-(2,2,6,6-tetramethyl-cyclohex-1-yloxy)-butan-2-ol

Starting materials:
2,2,6,6-tetramethyl-cyclohexanol
1,2-epoxy-butane.
IR: 3440 cm$^{-1}$;
NMR: signals at 1.0; 2.67 and 3.45–3.9 δ ppm;
MS: M$^+$=228(1); m/e: 138(21), 109(24), 82(100), 69(28), 55(22), 41(20).

(f) 1-(2,2,6,6-tetramethyl-cyclohex-1-yloxy)-pentan-2-ol

Starting materials:
2,2,6,6-tetramethyl-cyclohexanone
1,2-epoxy-pentane.
IR: 3460 cm$^{-1}$;
NMR: signals at 0.95; 2.67 and 3.4–4.0 δ ppm;
MS: M$^+$=242(1); m/e: 138(21), 109(22), 82(100), 69(31), 55(14), 41(21).

(g) 1-(2,2,6,6-tetramethyl-cyclohex-1-yloxy)-hexan-2-ol

Starting materials:
2,2,6,6-tetramethyl-cyclohexanol
1,2-epoxy-hexane.
IR: 3450 cm$^{-1}$;
NMR: signals at 0.95; 2.38 and 3.4–4.0 δ ppm;
MS: M$^+$=256(1); m/e: 138(20), 109(24), 82(100), 69(30), 55(25), 41(31).

(h)
1-(2,5,6,6-tetramethyl-cyclohex-1-yloxy)-pentan-2-ol

Starting materials:
2,5,6,6-tetramethyl-cyclohexanol
1,2-epoxy-pentane.
IR: 3450 cm$^{-1}$;
NMR: signals at 0.9; 2.41 and 3.1–4.0 δ ppm;
MS: M$^+$=242(42); m/e: 157(22), 138(99), 123(40), 109(22), 96(54), 83(95), 69(100), 55(90), 41(93).

Olfactive evaluation: characteristic wood-ambery; animal note of natural amber type; powerful and tenacious.

(i)
1-(2-ethyl-6,6-dimethyl-cyclohex-1-yloxy)-pentan-2-ol

Starting materials:
2-ethyl-6,6-dimethyl-cyclohexanol
1,2-epoxy-pentane.
IR: 3450 cm$^{-1}$;
NMR: signals at 0.9; 2.53 and 3.2–4.0 δ ppm;
MS: M$^+$=242(67); m/e: 171(22), 139(22), 109(35), 82(100), 69(78), 55(62), 41(79).

Olfactive evaluation: woody-ambery; less powerful than h).

(j) 1-(t-2,t-6-dimethyl-r-1-cyclohexyloxy)-pentan-2-ol

Starting materials:
t-2,t-6-dimethyl-cyclohexanol
1,2-epoxy-pentane.
NMR (90 MHz): 0.99; 2.5; 3.25–3.95 δ ppm;
MS: M$^+$=214(27); m/e: 111(100), 71(57), 69(97), 55(58), 41(40).

Olfactive evaluation: slightly woody.

(k) 1-(c-2,t-6-dimethyl-r-1-cyclohexyloxy)-pentan-2-ol

Starting materials:
c-2,t-6-dimethyl-cyclohexanol
1,2-epoxy-pentane.
NMR (90 MHz): 0.90 and 0.94; 2.8–3.9 δ ppm;
MS: M$^+$=214(22); m/e: 111(100), 71(38), 69(83), 55(44), 41(29).

Olfactive evaluation: woody; perspiration.

EXAMPLE 3

A base perfume composition for men cologne was prepared by mixing the following ingredients:

| Ingredients | Parts by weight |
|---|---|
| Synthetic bergamot oil | 150 |
| Cedryl acetate | 150 |
| Galbanum resinoid | 100 |
| Italian lemon oil | 80 |
| Discolourized oak moss absolute 10%* | 80 |
| Clove oil | 60 |
| EXALTEX ®[1] | 40 |
| Musk ketone | 40 |
| Lavender oil | 40 |
| Angelica roots oil 10%* | 40 |
| Clary sage oil | 30 |
| Neroli bigarade | 20 |
| Guinea orange oil | 20 |
| Basilicum oil 10%* | 20 |
| Synthetic jasmine absolute | 10 |
| FIXATEUR 404[1] 10%* | 10 |
| Labdanum kyst oil 10%* | 10 |
| Red thyme oil 10%* | 10 |
| Armoise oil | 10 |
| Total | 920 |

*in diethyl phthalate
[1]origin: Firmenich SA, Geneva (Switzerland)

The thus obtained perfume base composition can be qualified as woody-citrus like. A novel compositon was prepared by adding to 920 g of the above base 80 g of 1-(2,6,6-trimethyl-cyclohex-1-yloxy)-pentan-2-ol. This composition possessed a richer and more harmonious scent than the base composition and it possessed moreover a more elegant woody tonality. By replacing in the above example the mentioned ingredient by identical amounts of some of the compounds cited in Example 2, one can observe the following:

1-(2,6,6-trimethyl-cyclohex-1-yloxy)-butan-2-ol: analogous effect; slightly less pronounced
1-(2,6,6-trimethyl-cyclohex-3-en-1-yloxy)-pentan-2-ol: good woody effect, rich
1-(2,5,6,6-tetramethyl-cyclohex-1-yloxy)-pentan-2-ol: very elegant, woody effect, more pronounced than the above compound
1-(2-ethyl-6,6-dimethyl-cyclohex-1-yloxy)-pentan-2-ol: good woody effect, slightly less pronounced

EXAMPLE 4

100 G of a mixture of tobaccos of "American blend" type were sprayed with 10 g of a solution of 1-(2,6,6-trimethyl-cyclohex-1-yloxy)-pentan-2-ol at 0.01% in 95% ethanol. The thus treated tobacco mixture was used to manufacture test cigarettes, the smoke of which was subjected to an organoleptic evaluation by a panel of experts. The test cigarettes presented on smoking a more pronounced woody ambery gustative character than those manufactured with unflavored tobacco. Their taste and aroma were reminiscent of the smoke developed by cigarettes manufacture with oriental tobacco blends. By replacing in the above example 1-(2,6,6-trimethyl-cyclohex-1-yloxy)-pentan-2-ol by an identical amount of 1-(2,5,6,6-tetramethyl-cyclohex-1-yloxy)-pentan-2-ol, an identical effect was observed.

What we claim is:

1. A compound of formula

$$X-CH_2-CH(OH)-CH_2-R \qquad (I)$$

wherein symbol R represents a $C_1$–$C_3$ alkyl radical and X a substituted cyclohexyloxy group of formula

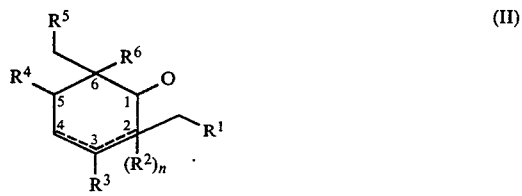

wherein index n stands for 0 or 1, the dashed lines indicated a single bond (n=1) or a double bond in position 2 (n=0) or 3 (n=1) and each of symbols $R^1$ to $R^6$ designates a hydrogen atom or a methyl radical.

2. A compound according to claim 1 selected from the group:
1-(2,6,6-trimethyl-cyclohex-1-yloxy)-pentan-2-ol,
1-(2,6,6-trimethyl-cyclohex-3-en-1-yloxy)-pentan-2-ol,
1-(2,3,6,6-tetramethyl-cyclohex-1-yloxy)-pentan-2-ol,
1-(2,5,6,6-tetramethyl-cyclohex-1-yloxy)-pentan-2-ol,
1-(2-ethyl-6,6-dimethyl-cyclohex-1-yloxy)-pentan-2-ol and
1-(2,6,6-trimethyl-cyclohex-1-yloxy)-butan-2-ol.

* * * * *